(12) United States Patent
Lannfelt et al.

(10) Patent No.: US 7,179,463 B2
(45) Date of Patent: Feb. 20, 2007

(54) TREATMENT OF ALZHEIMER'S DISEASE

(75) Inventors: Lars Lannfelt, Vintertullstorget 28, 11643 Stockholm (SE); Camilla Nilsberth, Norrköping (SE); Anita Westlind-Danielsson, Höllviken (SE); Jan Näslund, Stockholm (SE)

(73) Assignee: Lars Lannfelt, Stockholm (SE)

( * ) Notice: Subject to any disclaimer, the term of this patent is extended or adjusted under 35 U.S.C. 154(b) by 0 days.

(21) Appl. No.: 09/899,815

(22) Filed: Jul. 9, 2001

(65) Prior Publication Data

US 2002/0162129 A1 Oct. 31, 2002

Related U.S. Application Data

(60) Provisional application No. 60/217,098, filed on Jul. 10, 2000.

(30) Foreign Application Priority Data

Jul. 7, 2000 (EP) .................................. 00202387

(51) Int. Cl.
*A61K 39/395* (2006.01)
*A61K 39/40* (2006.01)
*A61K 39/42* (2006.01)
*A01N 37/18* (2006.01)
*C07K 16/00* (2006.01)

(52) U.S. Cl. .............................. 424/139.1; 424/130.1; 424/133.1; 424/141.1; 424/142.1; 424/145.1; 424/158.1; 514/2; 514/12; 530/387.1; 530/388.1; 530/388.15; 530/388.24

(58) Field of Classification Search ............. 424/139.1, 424/185.1, 9.2, 130.1; 530/300; 514/2
See application file for complete search history.

(56) References Cited

U.S. PATENT DOCUMENTS 5,854,204 A  12/1998  Findeis et al.

FOREIGN PATENT DOCUMENTS

| WO | WO 9511994 A1 | 5/1995 |
|---|---|---|
| WO | WO 9531996 A1 | 11/1995 |
| WO | WO 9927944 A1 | 6/1999 |
| WO | WO 0039310 A1 | 7/2000 |
| WO | WO 0072876 A2 | 12/2000 |

OTHER PUBLICATIONS

Vickers, 2002, Drugs Aging, 19(7), pp. 487-494.*
Schenk, et al., Immunization with amyloid-β attenuates Alzheimer-disease-like pathology in the PDAPP, Letters to Nature, 400:173-177 (Jul. 8, 1999).
St. George-Hyslop, et al., Genetic linkage studies suggest that Alzheimer's disease is not a single homogeneous disorder, Letters to Nature, 347:194-197 (Sep. 13, 1990).
Wirak, et al., Deposits of Amyloid β Protein in the Central Nervous System of Transgenic Mice, Science, 253:323-325 (Jul. 19, 1991).
St. George-Hyslop, et al., The Genetic Defect Causing Familial Alzheimer's Disease Maps on Chromosome 21, Science, 235:885-890 (Feb. 20, 1987).
Walsh, et al., Amyloid β-Protein Fibrillogenesis, The Journal of Biological Chemistry, 272(35):22364-22372 (Aug. 29, 1997).
Weidemann, et al., Identification, Biogenesis, and Localization of Precursors of Alzheimer's Disease A4 Amyloid Protein, Cell 57:115-126 (Apr. 7, 1989).
Giulian, et al., The HHQK Domain of β-Amyloid Provides a Structural Basis for the Immunopathology of Alzheimer's Disease, The Journal of Biological Chemistry, 273(45):29719-29726 (Nov. 6, 1998).
Palmert, et al., The β-amyloid protein precursor of Alzheimer disease has soluble derivatives found in human brain and cerebrospinal fluid, Proc. Natl. Acad. Sci. USA, 86:6338-6342 (Aug. 1989).
Levy, et al., Mutation of the Alzheimer's Disease Amyloid Gene in Hereditary Cerebral Hemorrhage, Dutch Type, Science, 248:1124-1126 (Jun. 1, 1990).
Conway, et al., Acceleration of oligomerization, not fibrillization, is a shared property of both α-synuclein mutations linked to early-onset Parkinson's disease: Implications for pathogenesis and therapy, PNAS, 97(2):571-576 (Jan. 18, 2000).
Mullan, et al., A pathogenic mutation for probable Alzheimer's disease in the APP gene at the N-terminus of β-amyloid, Nature Genetics, 1:345-347 (Aug. 1992).
Hendriks, et al., Presenile dementia and cerebral haemorrhage linked to a mutation at codon 692 of the β-amyloid precursor protein gene, Nature Genetics, 1:218-221 (Jun. 1992).
De Jonghe, et al., Flemish and Dutch Mutations in Amyloid β Precursor Protein Have Different Effects on Amyloid β Secretion, Neurobiology of Disease, 5:281-286 (accepted for publ., Aug. 19, 1998).
Kamino, et al., Linkage and Mutational Analysis of Familial Alzheimer Disease Kindreds for the APP Gene Region, Am. J. Hum. Genet. 51:998-1014 (revision recieved Jul. 24, 1992).
Citron, et al., Mutant presenilins of Alzheimer's disease increase production of 42-residue amyloid β-protein in both transfected cells and transgenic mice, Nature Medicine, 3(1):67-72 (Jan. 1997).
Forsell, et al., Amyloid precursor protein mutation at codon 713 (Ala—Val) does not cause schizophrenia: non-pathogenic variant found at codon 705 (silent), Neuroscience Letters, 184:90-93 (accepted Nov. 18, 1994).
Hardy, Amyloid, the presenilins and Alzheimer's disease, Trends Neurosci., 20(4):154-159 (1997).
Grabowski, et al., Novel Amyloid Precursor Protein Mutation in an Iowa Family with Dementia and Severe Cerebral Amyloid Angiopathy, Ann. Neurol., 49:697-705 (published online Mar. 19, 2001).

(Continued)

*Primary Examiner*—Olga N. Chernyshev
(74) *Attorney, Agent, or Firm*—Young & Thompson

(57) ABSTRACT

A method for the treatment of Alzheimer's disease in a subject having or suspected of having Alzheimer's disease by administering to the subject a therapeutically effective amount of an antibody wherein the antibody is raised against a protofibril that contains an Aβ-Arc peptide.

18 Claims, 2 Drawing Sheets

OTHER PUBLICATIONS

Scheuner, et al., Secreted amyloid β-protein similar to that in the senile plaques of Alzheimer's disease is increased *In vivo* by the presenilin 1 and 2 and *APP* mutations linked to familial Alzheimer's disease, Nature Medicine, 2(8):864-870 (Aug. 1996).

Serpell, Alzheimer's amyloid fibrils: structure and assembly, Biochimica et Biophysica Acta, 1502:16-30 (accepted Nov. 24, 1999).

Harper, et al., Assembly of Aβ Amyloid Protofibrils: An in Vitro Model for a Possible Early Event in Alzheimer's Disease, Biochemistry, 38:8972-8980 (published online Jun. 18, 1999).

Bacskai, et al., Imaging of amyloid-β deposits in brains of living mice permits direct observation of clearance of plaques with immunotherapy, Nature Medicine, 7(3):369-372 (Mar. 2001).

Frenkel, et al., Immunization against Alzheimer's β-amyloid plaques via EFRH phage administration, PNAS, 97(21):11455-11459 (Oct. 10, 2000).

Bard, et al., Peripherally administered antibodies against amyloid β-peptide enter the central nervous system and reduce pathology in a mouse model of Alzheimer disease, Nature Medicine, 6(8):916-919 (Aug. 2000).

Morgan, et al., Aβ peptide vaccination prevents memory loss in an animal model of Alzheimer's disease, Nature, 408:982-985 (Dec. 2000).

Janus, et al., Aβ peptide immunization reduces behavioural impairment and plaques in a model of Alzheimer's disease, Nature, 408:979-982 (Dec. 2000).

Chen, et al., A learning deficit related to age and β-amyloid plaques in a mouse model of Alzheimer's disease, Nature, 408:975-978 (Dec. 2000).

Nilsberth, et al., *A Novel APP Muatation (E693G)—The Arctic Mutation, Causing, Alzheimer's Disease with Vascular Symptoms,* Society for Neuiroscience Annual Meeting, Miami Beach, Abstract, Nov. 1999.

* cited by examiner

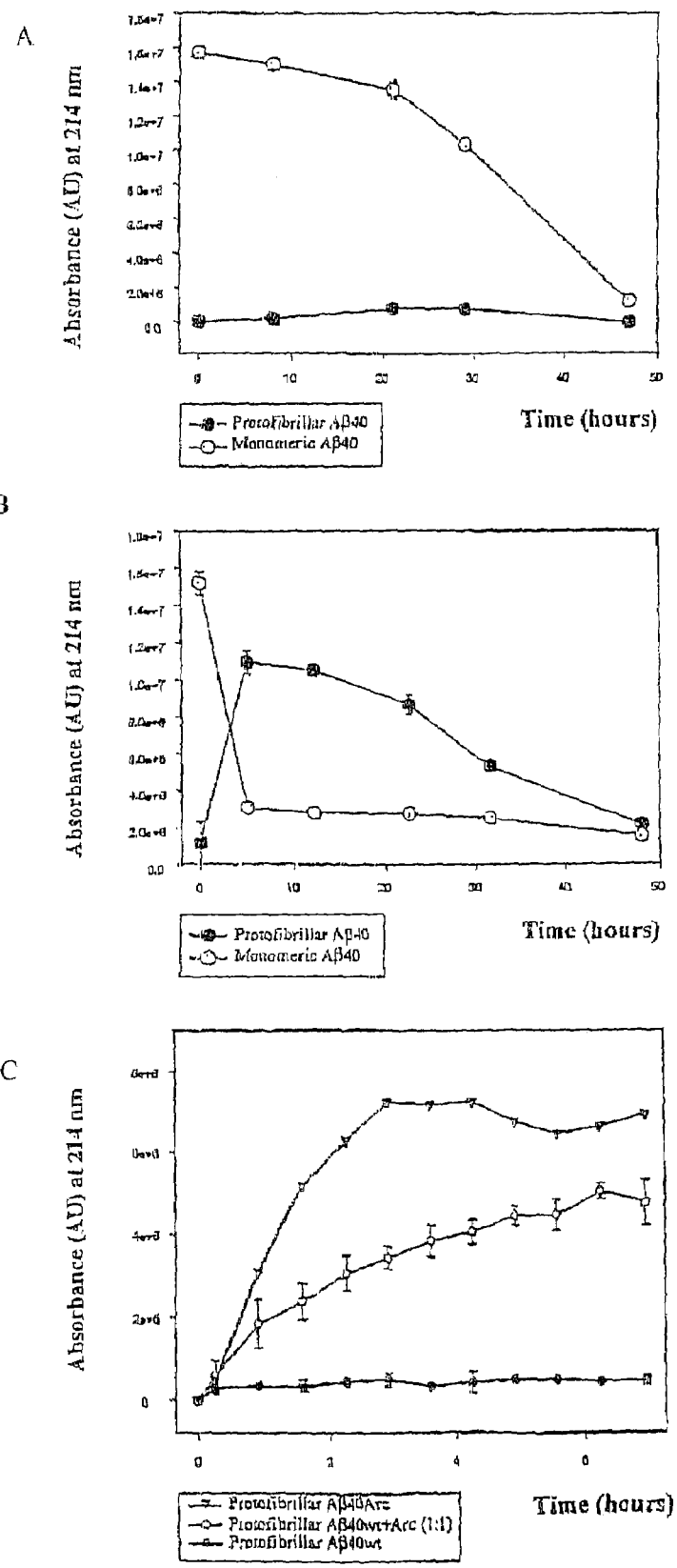
Fig. 1 A-C

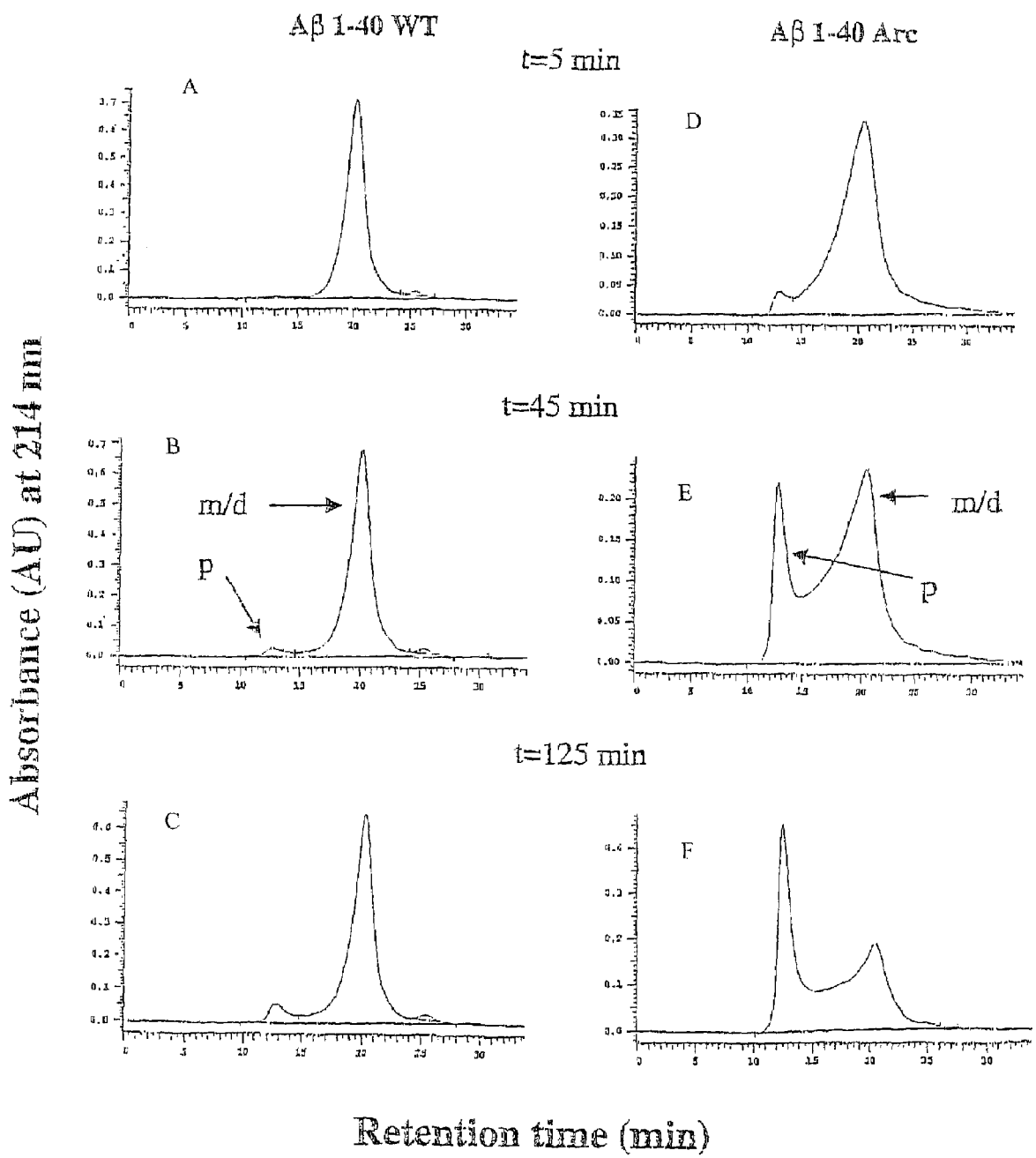
Fig. 2 A-F

TREATMENT OF ALZHEIMER'S DISEASE

This application claims priority to U.S. provisional application No. 60/217,098 filed Jul. 10, 2000.

FIELD OF THE INVENTION

The present invention relates to prevention and treatment of Alzheimer's disease (AD). More specifically, the invention relates to use of a non-wild type protofibril or compound(s) with protofibril forming ability for active immunisation in the purpose of treating or preventing AD. The invention further relates to a peptide, Aβ-Arc, with high protofibril forming activity as well as several applications thereof, such as antibodies against said peptide for passive immunisation against AD.

BACKGROUND OF THE INVENTION

Alzheimer's disease (AD) is a progressive disease known generally as senile dementia. The disease falls into two categories, namely late onset and early onset. One form of this latter AD type runs in families and it is known as familial AD.

Both types of AD are characterized by two types of lesions in the brain: senile plaques and neurofibrillary tangles. Senile plaques are areas of disorganized neuropil up to 150 mm across with extracellular amyloid deposits at the center. Neurofibrillary tangles are intracellular deposits consisting of two filaments twisted about each other in pairs.

Aβ also referred to as amyloid β peptide (AβP) is a highly aggregating small polypeptide having a molecular weight of approximately 4,500. This protein is a cleavage product of a much larger precursor protein referred to as amyloid precursor protein (APP). The Aβ protein comprises 39–42 amino acids (SEQ ID NO:1). There are at least five distinct isoforms of APP: 563, 695, 714, 751, and 770 amino acids, respectively (Wirak et al. (1991)). The Aβ protein segment comprises approximately half of the transmembrane domain and approximately the first 28 amino acids of the extracellular domain of an APP isoform.

APP is a transmembrane protein which is highly expressed in all parts of the body, and which has several important biological functions. Proteolytic processing of APP in vivo is a normal physiological process. Carboxy-terminal truncated forms of APP695, APP751, and APP770 are present in brain and cerebrospinal fluid (Palmert et al. (1989)) (Weidemann et al (1989)). There are probably two main metabolic pathways; one non-amyloid-forming and one amyloid-forming pathway. The amyloid forming non-normal pathway produces the Aβ protein polypeptide which is prone to form dense amyloidogenic aggregates that are resistant to proteolytic degradation and removal. The resultant Aβ protein aggregates presumably are involved in the formation of the abundant amyloid plaques and cerebrovascular amyloid that are the neuropathological hallmarks of AD.

In AD brains, the Aβ peptide forms virtually insoluble amyloid fibrils that accumulate into senile plaques. The Aβ fibrillization process is a complex multistep reaction. A group of distinct intermediary Aβ species of the fibrillization reaction, the protofibrils, were recently identified (Walsh et al. (1997)), (Walsh et al. (1999), (Harper et al,(1999)).

The most common Aβ form in cerebrospinal fluid (CSF) and plasma comprises 40 amino acids (Aβ40), but an Aβ comprising 42 amino acids (Aβ42) is the most common form in plaques (Scheuner et al. (1996)). This longer form tends to aggregate more rapidly and it is believed that it is more pathogenic than Aβ40.

Many patients get Alzheimer's disease spontaneously with unknown ethiology, but there are also several hereditary components involved. Disease-causing mutations in genes on chromosomes 1, 14, and 21, respectively, have been discovered, and these mutations might explain as much as 50% of disease forms starting very early (<50 years)(St. George-Hyslop et al. (1987), (Sherrington et al. (1995)).

The first gene associated with Alzheimer's disease was the gene encoding the amyloid precursor protein APP on chromosome 21. Different mutations of this gene result in unusual hereditary forms of the disease. Several pathogenic mutations have been identified in the (APP) gene, all located close to the major APP processing sites. These processing sites are either located adjacent to the boundaries of the Aβ domain in APP (the β- and γ-secretase sites) or within the Aβ sequence itself (α-secretase site).

The only known AD mutation close to the β-secretase site, the Swedish mutation (Mullan, et al., (1992)), discloses a double mutation (Lys670Asn/Met67ILeu) of the APP gene in a large Swedish family, in which family the disease starts early and has a high penetrating power. The mutation produces a large increase of Aβ production, an elevation of both Aβ42 and Aβ40 in plasma from mutation carriers and in conditioned cell media.

Other APP mutations have been described. All result in Alzheimer's disease with, an early age of onset having an autosomal dominant heredity pattern. Pathogenic mutations within the Aβ sequences located close to the α-secretase site, result in a phenotype different from AD, with massive amyloid accumulation in cerebral blood vessel walls. Two mutations at codons 692 and 693, namely the Dutch (Glu693Gln) and the Flemish (Ala692Gly) mutations, have been reported (Levy et al. (1990)), (van Broeckhoven et al. (1990)), (Hendriks et al. (1992)). Patients having these mutations suffer from cerebral haemorrhage and vascular symptoms. The vascular symptoms are caused by aggregation of Aβ in blood vessel walls (amyloid angiopathy). A third pathogenic intra-Aβ mutation was recently discovered in an Italian family (E693K), with clinical findings similar to the Dutch patients (Tagliavini, et al. (1999)).

Different pathogenic mechanisms have been proposed for the Dutch and Flemish mutations. It has been observed that the Flemish mutation leads to increased Aβ levels while a reduced ratio of Aβ42/40 was seen in media from cells transfected with the Dutch mutation (De Jonghe, et al. (1998)). Investigations of synthetic Aβ peptides have indicated that the Dutch mutation, but not the Flemish, accelerates the fibril formation compared to wild-type (wt) peptide (Walsh et al. (1997)).

As reported by Kamino et al. 1992, another APP E693 variant wherein Glu is substituted for Gly at APP E693, has previously been seen in one individual. It could not be unambiguously determined to be responsible for AD, though. This case originated from a family with similar clinical characteristics for AD and definitive AD was confirmed at autopsy. However, in this family the mutation could only be detected in one of two demented siblings.

Mice transgenic for APP mutations show many of the pathological features of Alzheimer disease, including deposition of extracellular amyloid plaques, astrocytosis and neuritic dystrophy. In recent studies by (Schenk et al (1999)) it was reported that immunization with Aβ42 wild-type peptide is both preventive in transgenic mice, but also that Aβ containing plaques can be greatly reduced in the brain of transgenic mice immunized with the peptide.

However, due to the large costs and suffering that are associated with Alzheimer's disease, there is still a need for improved methods for treatment and prevention thereof.

Likewise, there is a need For a method for screening compounds that could constitute a part of future pharmaceutical preparations for treating and perhaps curing Alzheimer's disease.

SUMMARY OF THE INVENTION

The present invention relates to an active immunisation against AD which will have a much more profound effect in the treatment of Alzheimer's disease, than using the wild-type peptide. Immunization according to the invention will yield antibodies directed to protofibrils, as the immunogen is a protofibril or compound(s) with greatly increased protofibril formation properties. These antibodies, generated in the periphery, will cross the blood brain barrier and mediate clearance of Aβ in the brain in a protofibril state.

In present invention use is made of a pathogenic AD mutation at codon 693 (Glu693Gly), named the 'Arctic mutation', located within the Aβ peptide domain of the APP gene, more closely position 22 of the Aβ-Arc peptide. Carriers of this mutation develop progressive dementia with clinical features typical of AD without symptoms of cerebrovascular disease. Said AD is distinctly characterised by accelerated formation of protofibrils comprising mutated Aβ peptides (40Arc and/or 42Arc) compared to protofibril formation of wild type Aβ peptides.

Thus, in a first aspect the invention relates to use of a non-wild type protofibril or compound(s) with protofibril forming ability for immunisation for prevention or treatment of Alzheimer's disease (AD). Preferably, these protofibril or compound(s) have enhanced protofibril forming ability and/ or enhanced immunogenicity compared to the wild-type counterparts. Protofibril chemistry has been described by, inter alia, Serpell (2000).

Preferably, the protofibril or compound(s) with protofibril forming ability comprises the following amino acid sequence KLVFFAEDV (SEQ ID NO:2). The Aβ 1–42 fibrillisation process involves transitional conformation changes from α-helix via random coil to β-sheet. The stable α-helix sequence of residues 16–24 (KLVFFAEDV (SEQ ID NO:2)) apparently plays an important role in this process.

The protofibril or compound(s) with protofibril forming ability may be mutated or modified in relation to corresponding wild-type counterparts. Changes in the KLVETAEDV (SEQ ID NO:2) sequence will affect the fibrillisation process. For example, changes of the charged amino acids Glu22 and Asp23 into neutral amino acids will induce a random coil structure in the Aβ peptide. Furthermore, deprotonation of other amino acids such as Asp7, Glu11 and His 6, 13 and 14 in the N-terminal end, has been suggested to destabilize the α-helix, leading to initiation of the fibrillation process. Another example is mutations leading to increased irninunogenicity in man by using amino acids from mouse Aβ at specific positions, e.g. Gly 5, Phe10 Arg13. Furthermore, amino acid 13 in Aβ is known to be part of a heparan sulphate binding motif (13–16; His, His, Gln, Lys) in human, which has been speculated to be involved in AD disease mechanism (inflammation) (Giulian et al. (1998)). In mouse, His 16 is exchanged for Arg 13 destroying the heparan sulphate binding site. Interestingly, mice have never been observed to develop AD. Hence, the use of Aβ-Arc/Arg13 as an immunogen would be a way to lower possible inflammatory side effects, elicited with Aβ peptides with intact heparan sulphate binding motif.

Preferably, the protofibril or compound(s) with protofibril forming ability comprises an Aβ peptide (β-amyloid protein) and repeats thereof, such as dimeric, oligomeric or multimeric forms). In a preferred embodiment the protofibril or compound(s) with protofibril forming ability comprises a Aβ peptide related to AD, In another embodiment the protofibril or compound(s) with protofibril forming ability comprises α-synuclein.

There exists a form of dementia characterised by patients having clusters in the brain of a structure called Lewy bodies. This form of dementia comprises about 20% of all dementia, Patients with Lewy bodies show, inter alia, Parkinson symptoms with progressive cognitive dysfunction. However, some patients also exhibit Alzheimer symptoms and this is called "Lewy variant of Alzheimer". The main component of the Lewy bodies is the protein α-synuclein. Two mutations in α-synuclein have been identified Ala53Thr and Ala30Pro. These mutations lead to dominant heritage of Parkinson's disease. These mutations affect the structure/solubility of α-synuclein and leads to formation of protofibrils. (Conway et al. (2000)).

The Aβ-Arc as disclosed in SEQ ID NO:1. Aβ-Arc comprises 39, 40 or 42 amino acids but may also be shorter as long as the protofibril forming ability is maintained.

The profibril or compound(s) with protofibril forming ability may be used in combination with Aβ peptides having known mutations, such as the Dutch, Flemish, Italian mutation described above as well as the Iowa mutation (D694N) (Grabowski et al., 2001). The Aβ peptide may comprise one or more of these and/or other mutations. Alternatively, a cocktail of different Aβ peptides with different mutations is used.

In a second aspect, the invention relates to a peptide, Aβ-Arc, having the amino acid sequence disclosed in SEQ ID NO 1 comprising a glycine at position 22 instead of glutamic acid compared to wild type Aβ peptide. The peptide may be natural, synthetic or recombinantly produced. For the purposes of the invention the peptide may be used in monomeric, dimeric, oligomeric, protofibril or multimeric form.

The invention also relates to nucleic acid encoding the above peptide as well as a vector comprising the nucleic acid. The vectors for expressing the polypeptides of the invention require that the nucleic acid be "operatively linked." A nucleic acid is operatively linked when it is placed into a functional relationship with another nucleic acid sequence.

This vector may be inserted in a host cell. Such a host cell can be used to recombinantly produce the peptide of the invention for pharmaceutical or diagnostic use as well for research purposes. The peptide may also be produced synthetically and be purified by HPLC, RP-HPLC, SEC-HPLC.

In a further aspect, the invention relates to a transgenic non-human animal comprising the above vector. Furthermore, the invention relates to a transgenic non-human animal comprising a vector comprising the entire APP gene corresponding to NCBI database, accession no XM_009710, Homo sapiens amyoid β (A4) precursor protein (protease nexin-II, Alzheimer's disease)(APP), mRNA. However, the APP gene for use in the invention comprises the Arctic mutation, i.e. nucleotide number 2225 is mutated from A to G leading to an amino acid substitution from Glutamic acid to Glycine. The transgenic animal may be used for modelling Alzheimer's disease and testing for therapeutic treatment efficacy. This transgenic animal will bear the entire APP gene comprising the Arctic mutation. This gene is preferably under control of a strong promoter, such as the prion-promoter. The APP gene may contain further mutations, besides the Arctic mutation.

The transgenic animal expresses a human APP or a fragment thereof which encodes glycine instead of glutamic acid at codon 693. Preferably, the animal expresses neuropathological characteristics of AD. Preferably, the mutated APP is expressed in cells which normally expresses the naturally-occurring endogenous APP gene (if present). Typically, the non-human animal is a mouse, Such transgenes typically comprises an Arctic mutation APP expression cassette, wherein a linked promoter and, preferably, an enhancer drive expression of structural sequences encoding a heterologous APP polypeptide comprising the Arctic mutation.

Such transgenic animals are usually produced by introducing the transgene or targeting construct into a fertilized egg or embryonic stem (ES) cell, typically by microinjection, electroporation, lipofection, or biolistics. The transgenic animals express the Arctic mutation APP gene of the transgene (or homologously recombined targeting construct), typically in brain tissue. Alzheimer phenotype and neuropathology is caused by protofibril formation. Such animals are suitable for use in a variety of disease models and drug screening uses, as well as other applications.

In yet a further aspect, the invention relates to antibodies against the Aβ peptide of SEQ ID NO:1. The antibodies may be monoclonal or polyclonal or antibody fragments, Preferably the antibodies are humanized for use in passive immunisation for prevention of therapy against AD. Thus, antibodies which react with the unique epitope created by glycine at codon 693 are provided.

Another aspect of the invention relates to a pharmaceutical composition, comprising the above peptide and physiologically acceptable excipients for human and veterinary use. The preparation may comprise adjuvants for vaccination purposes. The administration route may be s.c., i.m., oral or nasal.

In a further aspect, the invention relates to use of the above Aβ peptide for high throughput screening to find substances with anti-protofibrillar activity.

In a further aspect, the invention relates to a method for prevention or treatment of AD, comprising the step:
decreasing the formation of Aβ protofibrils and/or lower meric forms thereof in a subject having, or suspected of having, AD.

The decreasing step above may be by active immunisation with a profibril or compound(s) with protofibril forming ability for prevention or treatment of Alzheimer's disease (AD). wherein said protofibril or compound(s) have enhanced protofibril forming ability and/or enhanced immunogenicity compared to the wild-type counterparts.

Alternatively, the decreasing step above is by passive immunisation with antibodies against protofibrils or compound(s) with protofibril forming ability, such as Aβ-Arc, The passive immunisation may be in combination with antibodies against other Aβ peptides with mutations/modifications leading to increased protofibril formation and/or immunogenicity, preferably AD related mutations.

Antibodies generated against the human Aβ sequence containing the Arctic mutation are directed towards Aβ protofibrils and therefore are of therapeutic value in the treatment of Alzheimer's disease. Because the Aβ peptide is in a protofibril conformation when used as an immunogen, antibodies against Aβ protofibrils are generated. Availability of such antibodies opens Lip possibilities for the development of an efficient and lasting vaccination for the prevention and treatment of Alzheimer's disease.

In another alternative the decreasing step of the method according to the invention is by administration of agents with anti-protofibrillar activity.

In yet a further aspect of the invention, a combination of the vaccine or passive immunization with monoclonal antibodies or compounds with anti-fibrillar activity with one or several other AD treatments such as, acetylcholinesterase inhibitors, nootropics, anti-inflammatory drugs, estrogen, neurotrophic factor agonists, β-secretase inhibitors, γ-secretase inhibitors and α-secretase agonists, can improve AD treatment efficacy. The rational is that these substances/treatments work with completely different mechanisms of action and hence can be combined to the benefit for the AD patient.

DETAILED DESCRIPTION OF THE INVENTION

The basis of the present invention is a pathogenic amyloid precursor protein (APP) mutation located within the Aβ sequence at codon 693 (E693G), causing AD in a family from northern Sweden. Surprisingly, carriers of this "Arctic" mutation show decreased Aβ42 and Aβ40 levels in plasma. This finding is corroborated in vitro, where the Aβ42 concentration was low in conditioned media from cells transfected with $APP_{E693G}$. Fibrillization studies demonstrate that Aβ peptides with the Arctic mutation (Aβ40Arc) form protofibrils at a much higher rate and in larger quantities than wild-type (wt) Aβ (Aβ40wt). The unique Ending of decreased Aβ plasma levels in the Arctic AD family highlights the complexity of the disease and is likely to reflect a novel pathogenic mechanism. The mechanism disclosed in the present invention involves a rapid Aβ protofibril formation leading to accelerated build-up of insoluble Aβ intra- and/or extracellularly.

In the present invention, the single amino acid substitution Glu to Gly at position 22 in the Aβ4040Arc molecule was found to cause a dramatic increase in rate and capacity to form protofibrils compared to the Aβ40wt peptide. Thus, when Aβ42Arc and Aβ40Arc are formed in the brain it is likely that they are more prone to be retained by cellular systems since the accelerated drive to form protofibrils enhances both Aβ bulk and insolubility. Thus, factors promoting protofibril formation should be considered in the pathogenesis of sporadic AD. Increased protofibril formation is probably also operating in these more common forms of the disease. Indeed, the findings of the present invention open new avenues for possible therapeutic intervention using drugs targeted at preventing protofibril formation.

Studies on the Arctic mutation of the present invention have demonstrated a previously not described pathogenic mechanism for Alzheimer's disease through increased formation of Aβ protofibrils. Aβ with the Arctic mutation formed more stable protofibrils and at a much higher rate and in larger quantities than wild-type Aβ, even in the presence of equimolar amounts of wild-type Aβ. The formation is accelerated at least 2–10 times compared to protofibrill formation of wild type Aβ peptides. The implication of this finding is that the dangerous species in the amyloid forming pathway that eventually leads to Alzheimer's disease is not the Aβ fibrils, but a form of the peptide that appears earlier in the fibril maturation process, the protofibrils. One implication of the findings realted to the present invention is that it is important to prevent the formation of protofibrils in order to be able to prevent and treat Alzheimer's disease.

Non-human animals comprising transgenes which encode Arctic mutation APP can be used commercially to screen for agents having the effect of lowering the formation of Aβ protofibrils. Such agents can be developed as pharmaceuticals for treating abnormal APP processing and/or Alzheimer's disease amongst other neurodegenerative conditions in humans and animals, such as dogs. The transgenic animals of the present invention exhibit abnormal APP processing and expression, and can be used for pharmaceutical screening and as disease models for neurodegenerative diseases and APP biochemistry.

FIGURE LEGENDS

The present invention will now be further described with reference to the enclosed figures, in which:

FIG. 1 shows kinetics of soluble forms of Aβ1-40wt (a), Aβ1-40Arc (b) and protofibril formation of Aβ1-40wt, Aβ1-40Arc vs a mixture of Aβ1-40wt+Arc (1:1) (c), The Aβ1-40Arc peptide (92 µM) rapidly forms protofibrils (black dots) in comparison to the Aβ1-40wt peptide (88 µM), which mainly is in monomeric(dimeric (grey dots) form, data is taken from one experiment, representative of three (a and b). The protofibril formation rate was minitored during the first seven hours and the kinetics for the pure peptides (Aβ1-40wt and Aβ1-40Arc at 50 µM) was compared to the protofibril formation rate of a 1:1 mixture (50 µM) of Aβ1-40wt+Arc (c).

FIG. 2 depicts elution profiles showing Aβ40wt (a–c) versus Aβ40Arc (d–f) at 5 (a,d), 45 (b,e) and 125 (c,f) min of incubation. Accelerated protofibril (p) formation along with a parallel decline in the monomeric/dimeric (m/d) Aβ levels could be observed for Aβ40Arc (d–f) as compared to Aβ40wt (a–c). Data is from one experiment, representative of four. Initial peptide concentrations were 143 µM and 138 µM for Aβ40wt and Aβ40Arc, respectively.

EXAMPLES

The following examples are provided for illustration and are not intended to limit the invention to the specific example provided.

Example 1

Identification of the Arctic Mutation

An APP mutation (E693G) in a family from northern Sweden, named the "Arctic" family, is identified, which spans over four generations. The family was screened for mutations in exons 16 and 17 of the APP gene by single strand conformation polymorphism analysis (SSCP) (L. Forsell, L. Lannfelt, (1995)). An abnormal mobility pattern was observed in exon 17. Sequencing revealed an A→G nucleotide substitution, representing a glutamic acid to a glycine substitution at APP codon 693 (E693G), corresponding to position 22 in the Aβ sequence. Venous blood was drawn into tubes containing EDTA and DNA was prepared according to standard procedures. SSCP was performed. To sequence exon 17 of the APP gene a 319 bp fragment was amplified with the following primers 5'-CCT CAT CCA AAT GTC CCC GTC ATT-3' (SEQ ID NO:3) and 5'-GCC TAA TTC TCT CAT AGT CTT AAT TCC CAC-3' (SEQ ID NO:4). The PCR products were purified with QIAquick PCR purification kit (Qiagen) prior to sequencing. Direct sequencing was performed in both 3' and 5' direction using the same primers and the BIG Dye cycle sequencing protocol (PE Biosystems) and were then analyzed on an ABI377 automated sequencer (PE Biosystems). The Arctic mutation was seen in one family and not in 56 controls or 254 cases with dementia. Carriers of the arctic mutation showed no vascular symptoms. The mutation was further verified by restriction analysis, since it destroyed a MboII restriction site. The mutation was fully penetrant as no escapees were found. Two-point linkage analysis was performed between the mutation and affection status in the family with an age-dependent penetrance, giving a lod score of 3.66 at recombination fraction 0.00. Two-point lod score was calculated using Mlink from the linkage package (version 5.1) at each of the following recombination fractions 0.00, 0.10, 0.20, 0.30 and 0.40 (q males=q females). A single-locus model with an autosomal dominant inheritance was assumed, which was compatible with the inheritance as it appeared in the pedigree. A cumulative age dependent penetrance was assigned from the known ages of onset in the family. Individuals were put into different liability classes depending on the age at onset (affected) or age at last examination (unaffected). The disease gene frequency and the marker allele frequency were estimated to be 0.001 and the phenocopy rate was set to 0.0001.

Example 2

Clinical Symptoms in Carriers of the Arctic Mutation

The family with the "Arctic" mutation was clinically and genealogically investigated. In this family, the mean age of onset was 56.6 years and the mean duration of the disease was 7 years (n=5).

The first symptom in most cases in this family was an insidious loss of memory for recently acquired information. Symptoms before clinical manifestation of Alzheimer's disease were decreased power of concentration and difficulties in handling stress situations. All affected individuals in generation IV had an early retirement pension because of the disease. The patients in generation IV were investigated by magnetic resonance imaging (MRI), computed tomography (CT) and electroencephalography (EEG) which confirmed the diagnosis of Alzheimer's disease, In four individuals CT and MRI did not demonstrate signs of stroke or cerebral haemorrhage.

Example 3

Decreased Aβ Plasma Levels in Carriers of the Arctic Mutation

Pathogenic APP mutations have been shown to affect APP processing, as reflected in an increase of either total Aβ or Aβ42 in the plasma of affected family members. The Arctic mutation is located in a region different from other AD-causing mutations. It was investigated as to whether the mutation manifested itself by affecting Aβ plasma levels. Plasma from nine mutation carriers, of which four were symptomatic, and eleven non-carriers in the family, were analysed by well-characterized sandwich ELISA systems, specifically detecting Aβ42 (BAN50/BC05) and Aβ40 (BAN50/BA27) (Suzuki et al. 1994)), To reassure that the Arctic mutation did not change any of the antibody recognition sites Aβ40wt and Aβ40Arc peptides were tested and found to be recognized equally well. Furthermore, plasma was spiked with synthetic peptides, revealing that both AβArc and Aβwt peptides were recovered by ELISA to the same extent. The data obtained was analyzed by non-parametric Mann-Whitney analysis. The Aβ42 plasma concentration was 11.7±3.9 fmol/ml and 16.0±5.6 fmol/ml in mutation carriers and non-carriers, respectively, representing a 27% reduction of Aβ42 in the mutation carriers (p=0.04). The Aβ40 plasma concentration was 105±22 fmol/ml and 141±34 fmol/ml in mutation carriers and non-carriers, respectively, representing a 26% reduction of Aβ40 in the mutation carriers (p=0.01). The Aβ42/40 ratio was calculated for each individual, but no significant difference was found (p=0.13). In conclusion, concentrations of both Aβ42 and Aβ40 were unexpectedly and significantly reduced in individuals carrying the Arctic mutation.

Example 4

Aβ Levels in Cell Culture

The effect of the Arctic mutation on Aβ formation was further investigated in vitro in transiently transfected HEK293 cells. APPwt was compared to the following mutations: Arctic ($APP_{E693G}$), Dutch ($APP_{E693Q}$), Italian ($APP_{E693K}$) and Flemish ($APP_{A692G}$). Constructs containing the Swedish double mutation ($APP_{Swe}$) and one APP mutation at codon 717 ($APP_{V717F}$), both with well-studied APP processing characteristics (Hardy (1997)), were used as positive controls. The mutations were introduced to APP695 cDNA in pcDNA3 using QuikChange™ Site-Directed Mutagenesis Kit according to the manufacturers instructions (Stratagene). The mutated constructs were verified by sequencing. For the ELISA measurements, HEK293 cells were seeded in six-well dishes and transfected with the different constructs using FuGENE™ 6 Transfection Reagent (Roche Diagnostics) according to the manufacturers instructions, 24 h after transfection, the cells were conditioned 48 h in OptiMEM containing 5% newborn calf serum. After withdrawal of the media for ELISA measurements, the APP expression in the cells were investigated by western blot using monoclonal antibody 22C11 (Roche Diagnostics). Media was conditioned and analyzed for Aβ levels by the same Aβ42- and Aβ40-specific sandwich ELISA systems as used for human plasma (Citron, et al. (1997)). The Aβ42 and Aβ40 concentrations and Aβ42/40 ratios are shown in Table 1.

TABLE 1

Aβ42/40 ratio and Aβ42 and Aβ40 levels in conditioned media from transiently transfected HEK293 cells

| APP constructs | Aβ42/40 ratio (%) ± SD | Aβ42 ± SD (fmol/ml) | Aβ40 ± SD (fmol/ml) |
| --- | --- | --- | --- |
| APPwt | 9.6 ± 0.7 | 13.8 ± 1.0 | 144 ± 6 |
| Arctic (E693G) | 7.5 ± 0.5* | 11.2 ± 0.6 | 149 ± 3 |
| Dutch (E693Q) | 6.6 ± 0.6* | 9.6 ± 0.7 | 147 ± 12 |
| Italian (E693K) | 6.4 ± 0.6* | 8.0 ± 0.7 | 126 ± 17 |
| Flemish (A692G) | 11.7 ± 1.6* | 27.0 ± 2.0 | 232 ± 25 |
| Mock (vector only) | 7.2 ± 2.4 | 2.1 ± 1.0 | 28 ± 5 |

*P = 0.004 in comparison to APPwt

Decreasing Aβ42/Aβ40 ratios could be seen with all mutations at APP 693 (Arctic, Dutch, Italian). This may be due to increased rate of intracellular protofibril formation.

Example 5

Effect of Arctic Mutation on Protofibril Formation

The effect of the single amino acid substitution (Glu22Gly) on amyloid fibrillization kinetics was investigated. Synthetic Aβ1-40 was dissolved in physiological buffer and incubated for different periods of time. After centrifugation, the soluble Aβ in the supernatant, both low molecular weight (monomeric/dimeric) Aβ and protofibrils, were separated and analyzed using size exclusion chromatography (SEC) with UV detection at 214 nm, The morphology of the sedimented insoluble Aβ was visualized using negative stain and transmission electron microscopy (TEM).

Aβ1-40wt was purchased from Bachem, Bübendorf, Switzerland or Biosource International/QCB (Camarillo, Calif., USA) and Aβ1-40Arc from Biosource International/QCB. The peptides were trifluoroacetic salts. They were stored at −20° C. All other chemicals were of highest purity available. Samples of each peptide were incubated, without agitation, at 30° C. in 50 mM $Na_2HPO_4 \cdot NaH_2PO_4$ (pH 7.4) containing 0.1 M NaCl, for various time-points. Initial peptide concentrations were within the range of 88–143 μM, and were similar for both peptides in each experiment. After centrifugation (17 900×g for 5 min at 16° C.) monomeric/dimeric and protofibrillar Aβ1-40, sampled from the supernatant, were separated using SEC. A Merck Hitachi D-7000 LaChrom HPLC system, having a diod array detector model L-7455, a L-7200 model autosampler and a model L-7100 pump, coupled to a Superdex 75 PC3.2/30 column (Amersham Pharmacia Biotech, Uppsala, Sweden), was used for the chromatographic separation and analysis. Samples were eluted at a flow rate of 0.08 ml/min (ambient temperature) using 50 mM $Na_2HPO_4$ $NaH_2PO_4$ (pH 7.4), 0.15 M NaCl. Chromatograms were obtained by measuring UV absorbance at 214 nm. Peak areas for monomeric/dimeric and protofibrillar Aβ were integrated using Merck-Hitachi Model D-7000 Chromatography Data Station Software. The mean of triplicate integrated peak values from the SEC measurements were used to generate each data point shown in FIGS. 1 and 2. In addition, a standard curve was produced by correlating integrated peak areas with peptide concentrations as determined by quantitative amino acid analysis. The concentrations of total (at t=0 h) and soluble peptides remaining in solution after centrifugation were calculated from the standard curve.

SEC analysis of freshly dissolved Aβ1-40wt generated a single elution peak at a retention time of about 20 min (FIG. 2a). This peak represented the monomeric/dimeric forms of Aβ1-40wt (Walsh et al. (1997)). With increasing incubation time a second distinct peak appeared in the gel-excluded fraction With a retention time of about 12 min. This earlier peak contained protofibrils (FIGS. 2b, c), as verified by ultracentrifugation, negative stain and TEM of Aβ1-40wt (data not shown), in line with previous findings (Walsh et al. (1997)). Similar retention times were obtained for the Aβ1-40Arc peptide (FIGS. 2d–f). However, Aβ40Arc generated protofibrils much faster and in larger quantities than Aβ40wt. Chromatograms from three early time-points of incubation illustrate this difference (FIG. 1). The monomeric/dimeric Aβ40Arc peak declined in parallel with the growth of the protofibrillar peak (FIGS. 2d–f). The maximum concentration (111 μM) of Aβ40Arc protofibrils was observed at 6.5 h.

Kinetic studies up to 48 h showed that Aβ1-40wt generated a small quantity of protofibrils with a maximum concentration at 25 h (FIG. 1a). In contrast, a rapid and significant formation of protofibrils was seen within the first 5 h of incubation with a simultaneous rapid decline in the concentration of the monomeric/dimeric Aβ1-40Arc peptide (FIG. 1b). Since carriers of the Arctic mutation are heterozygots they generate both Aβwt and AβArc, Assuming equimolar in vivo production, the kinetics of protofibril formation was studied in a 1:1 mixture of Aβ1-40wt and Aβ1-40Arc. This mixture of peptides showed kinetics that were intermediate to the single peptide curves (FIG. 1c).

Example 6

Morphology of Aβ-Arc

A typical fibrillar morphology of Aβ1-40Arc in sedimented samples from kinetic studies was confirmed by negative stain and TEM. Aβ peptide samples were prepared and incubated as indicated for the kinetic studies, using higher peptide concentrations (617 μM). After 8 days, aggregated Aβ species were sedimented using the same centrifugation parameters as described above. Buffer was removed and pelleted material was suspended in 50 μl water using gentle sonication (2×6 s). Eight μl samples were applied to carbon stabilized Formvar film grids (Ted Pella, Inc., Redding, Calif., USA). Samples were negatively stained with 8 μl uranyl acetate (1%) (E. Merck, Darmstadt, Germany). Four grids were prepared for each sample and examined using a Philips CM10 TEM. Samples from pellets sedimented during the kinetic experiments were also examined. Similar to the sedimented Aβ40wt, large mesh-works of Aβ could be seen in these preparations. Protofibrils could also be discerned in the sedimented samples. The Aβ1-40Arc protofibrils were longer and less curved compared to the Aβ1-40wt protofibrils. Inter-twining of several fibrils was more common in the Aβ40Arc preparations, resulting in larger fibril diameters.

Example 7

Kinetic Studies

Kinetic studies comparing the formation of Aβ40gly22 protofibrils in the presence of a high and a low concentration of NaCl:

The experiments examining Aβ40gly22 protofibril and fibril formation, have been performed in 50 mM phosphate buffer supplemented with 100 mM NaCl. They present data that show that the rate and magnitude of Aβ40gly22 protofibril formation is significantly enhanced in the presence of a high NaCl concentration. Since intra- and extra-neuronal NaCl concentrations differ significantly (ca117 mM vs 30 mM), this finding supports an increased ability of Aβ40gly22 to form protofibrils in the extra-neuronal space where β-amyloid plaques are found.

REFERENCES

Citron, et al. *Nature Med* 3, 67–72 (1997).
Conway, et al., *Proc Natl Acad Sci USA* 97, 571–576 (2000).
De Jonghe, et al., *Neurobiol Disease* 5, 281–286 (1998).
Forsell, Lannfelt, *Neurosci Lett* 184, 90–93 (1995).
Giulian et al., *J Biol Chem,* 273, 29719–19726, (1998).
Grabowski et al., *Ann Neurol* 49, 697–705 (2001)
Hardy, *Trends Neurosci.* 20, 154–159 (1997).
Harper et al., *Biochemistry* 38, 972–8980 (1999).
Hendriks, et al., *Nature Genet* 1, 218–221 (1992).
Kamino, et al., *Am J Hum Genet* 51, 998 1014 (1992).
Levy, et al., *Science* 248, 1124–1126 (1990).
Mullan, et al., *Nature Genet* 1, 345–347 (1992).
Palmert et al. *PNAS* 86:6338 (1989)
Schenk et al., *Nature,* 400, 173–177 (1999)
Scheuner, et al., *Nature Med* 2, 864–869 (1996).
Serpell L. C. *Biochim. Biophys. Acta,* 1502, 16–30 (2000).
Sherrington et al. *Nature* 375:754 (1995)
St. George-Hyslop et al. *Science* 235:885 (1987)
Suzuki, et al., *Science* 264, 1336–1340 (1994).
Tagliavini, et al., *Alz Report* 2, S28 (1999),
Walsh et al., *J Biol Chem* 272, 22364–22372 (1997).
Walsh et al., *J Biol Chem* 36, 25945–25952 (1999).
Weidemann et al. *Cell* 57:115 (1989)
Wirak et al. *Science* 253:323 (1991)

The invention claimed is:

1. A method for the treatment of Alzheimer's disease (AD) in a subject having or suspected of having AD, comprising administering to said subject a therapeutically effective amount of an antibody wherein said antibody is raised against a protofibril comprising an Aβ-Arc peptide selected from the group consisting of Aβ39-Arc (Amino Acids 1–39 of SEQ ID NO:1), Aβ40-Arc (Amino Acids 1–40 of SEQ ID NO:1), and Aβ42-Arc (SEQ ID NO:1), wherein said antibodies bind to arctic and wild-type Aβ peptides in protofibril conformation.

2. A method for the treatment of Alzheimer's disease (AD) in a subject having or suspected of having AD, comprising administering to said subject a therapeutically effective amount of an antibody, wherein said antibody is raised against a protofibril comprising an Aβ-Arc peptide selected from the group consisting of Aβ39-Arc (Amino Acids 1–39 of SEQ ID NO:1), Aβ40-Arc (Amino Acids 1–40 of SEQ ID NO:1), Aβ41-Arc (Amino Acids 1–41 of SEQ ID NO:1), Aβ42-Arc (SEQ ID NO:1), and combinations thereof, wherein said antibodies bind to arctic and wildtype Aβ peptides in protofibril conformation.

3. The method according to claim 2, wherein said protofibril further comprises an Aβ peptide having a mutation selected from the group consisting of the Dutch, Flemish, Italian, Iowa mutations, and combinations thereof.

4. The method according to claim 2, wherein said antibody is monoclonal.

5. The method according to claim 2, wherein said antibody is human or humanized.

6. The method according to claim 2, wherein said protofibril further comprises an Aβ peptide having a Dutch mutation.

7. The method according to claim 2, wherein said Aβ-Arc peptide is Aβ39-Arc (Amino Acids 1–39 of SEQ ID NO:1).

8. The method according to claim 2, wherein said Aβ-Arc peptide is Aβ40-Arc (Amino Acids 1–40 of SEQ ID NO:1).

9. The method according to claim 2, wherein said Aβ-Arc peptide is Aβ41-Arc (Amino Acids 1–41 of SEQ ID NO:1).

10. The method according to claim 2, wherein said Aβ-Arc peptide is Aβ42-Arc (SEQ ID NO:1).

11. A method for the treatment of Alzheimer's disease (AD) in a subject having or suspected of having AD, comprising administering to said subject a therapeutically effective amount of an antibody, wherein said antibody is raised against a composition comprising a protofibril comprising an Aβ-Arc peptide selected from the group consisting of Aβ39-Arc (Amino Acids 1–39 of SEQ ID NO:1), Aβ40-Arc (Amino Acids 1–40 of SEQ ID NO:1), Aβ41-Arc (Amino Acids 1–41 of SEQ ID NO:1), Aβ42-Arc (SEQ ID NO:1), and combinations thereof, wherein said antibodies bind to arctic and wild-type Aβ peptides in protofibril conformation.

12. The method according to claim 11, wherein said antibody is monoclonal.

13. The method according to claim 11, wherein said antibody is human or humanized.

14. The method according to claim 11, wherein said protofibril further comprises an Aβ peptide with a mutation selected from the group consisting of the Dutch, Flemish, Italian and Iowa mutations.

15. The method according to claim 11, wherein said Aβ-Arc peptide is Aβ39-Arc (Amino Acids 1–39 of SEQ ID NO:1).

16. The method according to claim 11, wherein said Aβ-Arc peptide is Aβ40-Arc (Amino Acids 1–40 of SEQ ID NO:1).

17. The method according to claim 11, wherein said Aβ-Arc peptide is Aβ-Arc (SEQ ID NO:1).

18. The method according to claim 11, wherein said Aβ-Arc peptide is Aβ41-Arc (Amino Acids 1–41 of SEQ ID NO:1).

* * * * *

UNITED STATES PATENT AND TRADEMARK OFFICE
CERTIFICATE OF CORRECTION

PATENT NO. : 7,179,463 B2 Page 1 of 1
APPLICATION NO. : 09/899815
DATED : February 20, 2007
INVENTOR(S) : Lars Lannfelt et al.

It is certified that error appears in the above-identified patent and that said Letters Patent is hereby corrected as shown below:

Col. 14, Line 59 – 60
Rewrite claim 17 as follows:

--The method according to claim 11, wherein said Aβ-Arc peptide is (Aβ42-Arc)(SEQ ID NO:1).--

Signed and Sealed this

Third Day of July, 2007

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Gly Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 9
<212> TYPE: PRT
<213> ORGANISM: Artificial Sequence
<220> FEATURE:
<223> OTHER INFORMATION: synthetic peptide   (16-24 of SEQ ID NO:1)
```

```
<400> SEQUENCE: 2

Lys Leu Val Phe Phe Ala Glu Asp Val
1               5

<210> SEQ ID NO 3
<211> LENGTH: 24
<212> TYPE: DNA
<213> ORGANISM: Artificial Sequence
<220> FEATURE:
<223> OTHER INFORMATION: primer #1 to sequence exon 17 of APP gene

<400> SEQUENCE: 3
cctcatccaa atgtccccgt catt                                          24

<210> SEQ ID NO 4
<211> LENGTH: 30
<212> TYPE: DNA
<213> ORGANISM: Artificial Sequence
<220> FEATURE:
<223> OTHER INFORMATION: primer #2 to sequence exon 17 of APP gene

<400> SEQUENCE: 4
gcctaattct ctcatagtct taattcccac                                    30
```